US012307825B2

(12) United States Patent
Urabe

(10) Patent No.: US 12,307,825 B2
(45) Date of Patent: May 20, 2025

(54) BIOMETRIC DETERMINATION DEVICE AND BIOMETRIC DETERMINATION METHOD

(71) Applicant: OMRON Corporation, Kyoto (JP)

(72) Inventor: Kazuya Urabe, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 340 days.

(21) Appl. No.: 17/921,196

(22) PCT Filed: Apr. 20, 2021

(86) PCT No.: PCT/JP2021/016080
§ 371 (c)(1),
(2) Date: Oct. 25, 2022

(87) PCT Pub. No.: WO2021/241083
PCT Pub. Date: Dec. 2, 2021

(65) Prior Publication Data
US 2023/0177886 A1    Jun. 8, 2023

(30) Foreign Application Priority Data

May 25, 2020  (JP) .................................. 2020-090358

(51) Int. Cl.
*G06V 40/40* (2022.01)
*G06V 10/22* (2022.01)
(Continued)

(52) U.S. Cl.
CPC .............. *G06V 40/40* (2022.01); *G06V 10/22* (2022.01); *G06V 40/15* (2022.01); *G06V 40/161* (2022.01)

(58) Field of Classification Search
CPC ........ G06V 40/40; G06V 10/22; G06V 40/15; G06V 40/161; G06V 40/16; G06V 40/166;
(Continued)

(56) References Cited

U.S. PATENT DOCUMENTS

| 2011/0267499 A1* | 11/2011 | Wan .................... H04N 23/6811 |
| | | 348/240.2 |
| 2015/0227781 A1 | 8/2015 | Morishita |

(Continued)

FOREIGN PATENT DOCUMENTS

| JP | 2007241402 A | 9/2007 |
| JP | 2008262305 A | 10/2008 |

(Continued)

OTHER PUBLICATIONS

International Search Report issued in Intl. Appln. No. PCT/JP2021/016080 mailed Jul. 6, 2021. English translation provided.

(Continued)

*Primary Examiner* — Nimesh Patel
(74) *Attorney, Agent, or Firm* — ROSSI, KIMMS & McDOWELL LLP

(57) ABSTRACT

A biometric determination device includes a detection unit configured to detect a face from an image captured; an acquisition unit configured to acquire information on the temperature of a face region, which is a region in which a face is detected by the detection unit, and the temperature of an extra-facial region, which is a region around the face region; and a determination unit configured to determine on the basis of information acquired by the acquisition unit that a face that is detected is a living body when the temperature of the face region is higher than the temperature of the extra-facial region by greater than or equal to a predetermined threshold, and that a face that is detected is not a (Continued)

living body when the temperature of the face region is not higher than the temperature of the extra-facial region by greater than or equal to the predetermined threshold.

8 Claims, 10 Drawing Sheets

(51) Int. Cl.
*G06V 40/10* (2022.01)
*G06V 40/16* (2022.01)

(58) Field of Classification Search
CPC .. G06V 40/172; G06V 40/168; G06V 40/171; G06V 10/25; G06V 40/103; G06V 40/165; G06V 10/764; G06V 10/82; G06V 40/45; G06V 10/42; G06V 10/44; G06V 40/20; G06V 40/18; G06V 20/46; A61B 5/1176; A61B 5/015; G03B 19/00; G03B 15/00; G07C 9/37; G01K 13/20; G01K 7/427; G01K 1/16; G01K 17/00; G01K 7/02; G01K 1/143; G01K 1/024; G01K 2219/00; G01J 5/0025; G01J 2005/0077; G01J 5/064; G01J 1/0266; G01J 1/4228; G01J 2005/0092; G01J 2005/123; G01J 3/0208; G01J 3/0237; G01J 3/2823; G01J 5/0806; G06T 2207/30201; G06T 7/11; G06T 7/70; G06T 2200/24; G06T 2207/10024; G06T 7/136; G06T 2207/10048; G06T 2207/20084; G06T 3/40; G06T 7/00; G06T 7/0012; G06T 7/73; G06T 11/00; G06T 13/20; G06T 7/194; G06T 7/80; G06T 13/40; G06T 2207/10004; G06T 2207/20081; G06T 2207/20112; G06T 2210/12; G06T 5/00; G06T 5/94; G06T 7/12; G06T 7/174; G06T 7/246; G06T 7/32

See application file for complete search history.

(56) References Cited

U.S. PATENT DOCUMENTS

| | | | |
|---|---|---|---|
| 2017/0105662 A1* | 4/2017 | Silawan | A61B 5/14542 |
| 2017/0337692 A1* | 11/2017 | Romanenko | G06T 7/593 |
| 2019/0114495 A1* | 4/2019 | Chang | G01J 5/10 |
| 2020/0050748 A1* | 2/2020 | Guo | G06F 21/12 |
| 2020/0351435 A1* | 11/2020 | Therkelsen | H04N 7/155 |

FOREIGN PATENT DOCUMENTS

| | | |
|---|---|---|
| JP | 2018169943 A | 11/2018 |
| JP | 6544244 B2 | 7/2019 |

OTHER PUBLICATIONS

Written Opinion issued in Intl. Appln. No. PCT/JP2021/016080 mailed Jul. 6, 2021. English translation provided.

* cited by examiner

BIOMETRIC DETERMINATION DEVICE AND BIOMETRIC DETERMINATION METHOD

TECHNICAL FIELD

The present invention relates to techniques for determining whether a face captured is that of a living body, such as a person, or a non-living body such as a picture or video, or a doll.

BACKGROUND ART

Authentication via PIN or password, etc., authentication via an object (authentication object) such as an IC card, and authentication via face (face authentication), etc., are known authentication techniques. With authentication via PIN or password, authentication cannot be performed if the PIN or password is forgotten; another concern is that the PIN or password may be leaked and used for malicious purposes. With authentication via an authentication object, authentication cannot be performed if the authentication object is not available; another concern is that the authentication object may be stolen and used for malicious purposes.

These sorts of problems are not a concern when it comes to face authentication; however, it is a concern that a picture, a video displayed on a display device such as a monitor or a tablet terminal, or a non-living body such as a mannequin or wax doll may be used for spoofing to breach face authentication.

Therefore, various techniques have been proposed for preventing a face authentication breach via spoofing. PTL 1, for example, proposes determining whether or not a frame exists around the face that is captured to determine whether or not aforesaid face is a spoof. PTL 2 proposes determining whether or not a face is a spoof on the basis of color changes of the face that is captured. PTL 3 proposes determining whether or not a face is a spoof on the basis of the distance to the face that is captured and the distance to the background. Besides the techniques proposed in PTLs 1-3, another technique proposed determines whether or not a face is a spoof by whether or not the face that is captured has eyes that are blinking.

CITATION LIST

Patent Literature

PTL 1: Japanese Patent Publication No. 2018-169943
PTL 2: Japanese Patent Number 6544244
PTL 3: Japanese Patent Publication No. 2007-241402

SUMMARY OF INVENTION

Technical Problem

Most times there is a frame around a picture or a display device. Therefore, the technique proposed in PTL 1 is capable of preventing a face authentication breach from spoofing that uses a picture, or a face authentication breach from spoofing that uses a video displayed on a display device. Despite that, the technique is unable to prevent a face authentication breach from spoofing that uses a doll. Additionally, without being limited to cases where the frame of a picture or display device appears in an image that captures the face, in some cases an existing technique may be unable to prevent a face authentication breach from spoofing that uses a picture or a video.

The color of the face appearing in a picture (static image) and the color of the face of a doll does not change (the color of those kinds of faces may change due to the surrounding light; however, those kinds of changes are not ecological changes). Therefore, the technique proposed in PTL 2 is capable of preventing a face authentication breach from spoofing that uses a picture or a doll. Despite that, the technique is unable to prevent a face authentication breach from spoofing that uses a video (dynamic image).

The distance to the face appearing in a picture and the distance to the background appearing in the picture is the same (these distances are both distances to the picture). Similarly, the distance to the face displayed on a display device and the distance to the background displayed on the display device are the same (these distances are both distances to the display device). Therefore, the technique proposed in PTL 3 is capable of preventing a face authentication breach from spoofing that uses a picture, or a face authentication breach from spoofing that uses a video displayed on a display device. Despite that, the technique is unable to prevent a face authentication breach from spoofing that uses a doll.

A face appearing in a picture (static image) or a doll such as a mannequin or a wax doll has eyes that do not blink. Therefore, existing techniques for determining the presence or absence of eyes that are blinking are capable of preventing a face authentication breach from spoofing that uses a picture or a doll. Despite that, these techniques are unable to prevent a face authentication breach from spoofing that uses a video (dynamic image).

Thus, the existing art is unable to determine with high accuracy whether a face captured is a living body, such as a person, or a non-living body such as a picture or video, or a doll, and in some cases cannot prevent a face authentication breach.

In light of the above conditions, the present invention aims to provide techniques capable of determining with high accuracy whether a face captured is a living body such as a person, or a non-living body such as a picture or video, or a doll, and preventing a face authentication breach.

Solution to Problem

To address the above aims, the present invention adopts the following configurations.

A first aspect of the present invention is to provide a biometric determination device that includes: a detection unit configured to detect a face from an image captured; an acquisition unit configured to acquire information on the temperature of a face region, which is a region in which a face is detected by the detection unit, and the temperature of an extra-facial region, which is a region around the face region; and a determination unit configured to determine on the basis of information acquired by the acquisition unit that a face that is detected is a living body when the temperature of the face region is higher than the temperature of the extra-facial region by greater than or equal to a predetermined threshold, and that a face that is detected is not a living body when the temperature of the face region is not higher than the temperature of the extra-facial region by greater than or equal to the predetermined threshold. The predetermined threshold may be established as desired by a user (e.g., the administrator of a biometric determination device), or may be a fixed value.

The temperature of a face that is a living body is typically a certain degree higher than the temperature around the face (the background). It is conceivable then that this kind of temperature difference does not occur when a picture or video, or a doll, or the like is used for spoofing. More specifically, the temperature of the face appearing in a picture, and the temperature of the background appearing in the picture are the same (these temperatures are both the temperature of the picture). Similarly, the temperature of a face displayed on a display device and the temperature of the background displayed on the display device are the same (these temperatures are both the temperature of the display device). The temperature of the face of a doll is different from the temperature of a face that is a living body; the temperature of the face of a doll in many cases approaches the temperature of around the face (the background) or may be lower than the temperature of around the face.

The above-described configuration allows for determining with high accuracy whether or not a face is a living body, and preventing a face authentication breach by taking as the determination reference whether or not the temperature of a face region is higher than the temperature of the extra-facial region by greater than or equal to a predetermined threshold. Specifically, a determination can be made that the face is a non-living body even if any of a picture or video, a doll, etc., is used for spoofing, making it possible to prevent a face authentication breach. Though it is conceivable to also have a configuration that determines whether or not the face is a living body from only the temperature of the face, it is conceivable that the temperature around the face considerably impacts the temperature of the face. Therefore, a highly accurate biometric determination can be performed with a configuration that employs the temperature of the face and the temperature around the face than a configuration that employs only the temperature of the face.

A setting unit configured to set the extra-facial region on the basis of the face region may also be included; the setting unit may set the region surrounding a face as the extra-facial region. More specifically, the face region may be a rectangular region, and the setting unit may set the extra-facial region as the region that excludes the face region from a rectangular region that is centered on the face region and is an enlargement of the face region such that the height of the rectangular region and the width of the rectangular region are each a predetermined multiple of the face region. The face region may be a rectangular region, and the setting unit may set the extra-facial region as the region that excludes the face region from a rectangular region that is centered on the face region and is an enlargement of the face region such that the length of a diagonal of the rectangular region is a predetermined multiple of the face region. The face region may be a circular region, and the setting unit may set the extra-facial region as the region that excludes the face region from a circular region that is centered on the face region and is an enlargement of the face region such that the radius of the circular region is a predetermined multiple of the face region. The setting unit may set the extra-facial region as the region that excludes the face region from a region that is centered on the face region and is an enlargement of the face region such that the area of the region is a predetermined multiple of the face region.

The setting unit may set a region located on the left and a region located on the right of the face region as the extra-facial region. More specifically, the setting unit may set the extra-facial region as two rectangular regions obtained by excluding the face region and a rectangular region of the face region with the same width as the upper part of the face region and a rectangular region of the face region with the same width as the lower part of the face region from a rectangular region that is centered on the face region and is an enlargement of the face region by a predetermined multiple. Herewith the head portion which is at the upper part of the face region and the neck portion which is at the lower part of the face region can be excluded from the extra-facial region, and a temperature closer to the temperature of the background may employed as the temperature of the extra-facial region. As a result, the determination of whether or not a face is a living body can be made with even higher accuracy, and face authentication can be performed with even higher accuracy. Specifically, this can prevent an erroneous determination that a face that is a living body is a non-living body, thus preventing a failure of proper face authentication using the face of a living body. The rectangular region, which is an enlargement of the face region by a predetermined multiple, may be any of an enlargement of the length of a diagonal of the face region by a predetermined multiple, or an enlargement of the area of the face region by a predetermined multiple.

The various magnifications are not particularly limited, and may be two to three times, for instance. These magnifications may be established as desired by the user or may be a fixed value.

The temperature of the face region may be the mean, mode, or median of a plurality of temperatures each corresponding to a plurality of locations in the face region; the temperature of the extra-facial region may be the mode or median of a plurality of temperatures each corresponding to a plurality of locations in the extra-facial region. Herewith, the determination of whether or not a face is a living body can be made with even higher accuracy, and face authentication can be performed with even higher accuracy. Thus, there is no longer the need to use the temperature of an object placed on the face (e.g., such as glasses put on the face), and the like, as the temperature of the face region, or the temperature of a heat source around the face (e.g., lighting) and the like as the temperature of the extra-facial region, for example. As a result, this can prevent an erroneous determination that a face that is a living body is a non-living body, preventing a failure of proper face authentication using the face of a living body.

When a plurality of faces is detected by the detection unit, the acquisition of information by the acquisition unit and the determination by the determination unit may be performed with regard to each of the plurality of faces. Herewith, the failure of face authentication for a face-based registrant can be prevented in situation where, for instance, the face-based registrant stands in front of a poster where a face appears or the face-based registrant is with a plurality of persons or a doll. A face-based registrant is a person whose face information (face information that is compared to a detected face, face image, etc.) is registered for the purpose of face authentication.

A face-based registrant who is about to perform face authentication tends to bring their face close to the camera and the face of aforesaid face-based registrant tends to appear very large within the image captured. Therefore, when a plurality of faces is detected by the detection unit, the acquisition of information by the acquisition unit and the determination by the determination unit may be performed with regard to the face that is the largest among the plurality of faces. Herewith, as well, the failure of face authentication for a face-based registrant can be prevented in situation where, for instance, the face-based registrant stands in front of a poster where a face appears or the face-based registrant is with a plurality of persons or a doll. Moreover, acquiring the temperature information and the biometric determination are limited to a specific face, thus reducing the processing load.

A face-based registrant who is about to perform face authentication tends to face front at the camera and the face of aforesaid face-based registrant tends to appear at the center portion of the image captured. Therefore, when a plurality of faces is detected by the detection unit, the acquisition of information by the acquisition unit and the determination by the determination unit may be performed with regard to the face that is the closest to the center of the image among the plurality of faces. Herewith, as well, the failure of face authentication for a face-based registrant can be prevented in situation where, for instance, the face-based registrant stands in front of a poster where a face appears or the face-based registrant is with a plurality of persons or a doll. Acquiring the temperature information and the biometric determination are limited to a specific face, thus reducing the processing load.

A face-based registrant who is about to perform face authentication tends to direct their gaze toward the camera. Therefore, when a plurality of faces is detected by the detection unit, the acquisition of information by the temperature information acquisition unit and the determination by the determination unit may be performed with regard to the face that has the gaze directed toward the camera capturing the image among the plurality of faces. Herewith, as well, the failure of face authentication for a face-based registrant can be prevented in situation where, for instance, the face-based registrant stands in front of a poster where a face appears or the face-based registrant is with a plurality of persons or a doll. Acquiring the temperature information and the biometric determination are limited to a specific face, thus reducing the processing load. It is also possible to prevent face authentication from being successful when unnecessary when a face-based registrant is near the camera without gazing at the camera (contrary to the intent of the face-based registrant), further improving the level of security of the face authentication.

A second aspect of the present invention is to provide a biometric determination method that includes: a detection step of detecting a face from an image captured; an acquisition step of acquiring information on the temperature of a face region, which is a region in which a face is detected during the detection step, and the temperature of an extra-facial region, which is a region around the face region; and a determination step of determining on the basis of information acquired during the acquisition step that a face that is detected is a living body when the temperature of the face region is higher than the temperature of the extra-facial region by greater than or equal to a predetermined threshold, and that a face that is detected is not a living body when the temperature of the face region is not higher than the temperature of the extra-facial region by greater than or equal to the predetermined threshold.

The present invention may be implemented as a biometric determination system having at least a portion of the above configurations or functions. The present invention may also be implemented as a biometric determination method or biometric determination system including at least a portion of the above processes; furthermore, the method may be implemented as a computer program for execution on a computer, or as a computer readable medium with the computer program permanently recorded thereon. The above-mentioned configurations and processes may be freely combined with each other insofar as is technically possible to configure the invention.

Advantageous Effects of Invention

The present invention is capable of determining with high accuracy whether a face captured is a living body, such as a person, or a non-living body such as a picture or video, or a doll, and preventing a face authentication breach.

DESCRIPTION OF EMBODIMENTS

Example Application

An example application of the present invention is described. The existing art is unable to determine with high accuracy whether a face captured is a living body, such as a person, or a non-living body such as a picture or video, or a doll, and in some cases cannot prevent a face authentication breach due to spoofing that uses a non-living body. Specifically, because at least any of a face appearing in a picture, a face appearing in a video, the face of a doll, or the like could be erroneously determined to be a living body, the existing art is not capable of preventing a face authentication breach due to spoofing that uses such kinds of non-living bodies.

Figure 1:
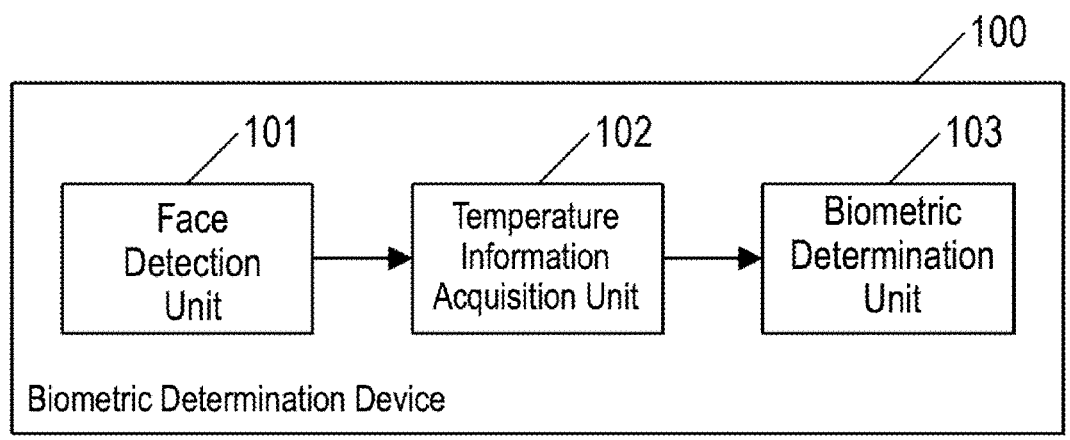
FIG. 1 is a block diagram illustrating an example configuration of a biometric determination device adopting the present invention.

FIG. 1 is a block diagram illustrating an example configuration of a biometric determination device 100 adopting the present invention; the biometric determination device 100 includes a face detection unit 101, a temperature information acquisition unit 102, and a biometric determination unit 103. The face detection unit 101 detects a face from an image captured. The temperature information acquisition unit 102 acquires information on the temperature of the face region, which is a region with a face detected by the face detection unit 101, and the temperature of an extra-facial region, which is a region around the face region. The biometric determination unit 103 determines whether or not the face detected by the face detection unit 101 is a living body on the basis of the temperature information acquired by the temperature information acquisition unit 102. Specifically the biometric determination unit 103 determines that the face detected is a living body when the temperature of the face region is higher than the temperature of the extra-facial region by greater than or equal to a predetermined threshold, and that the face detected is not a living body when the temperature of the face region is not higher than the temperature of the extra-facial region by greater than or equal to a predetermined threshold. The face detection unit 101 is one example of a detection unit in the present invention; the temperature information acquisition unit 102 is one example of an acquisition means of the present invention; and the biometric determination unit 103 is one example of a determination means of the present invention.

The temperature of a face that is a living body is typically a certain degree higher than the temperature around the face (the background). It is conceivable then that this kind of temperature difference does not occur when a picture or video, or a doll, or the like is used for spoofing. More specifically, the temperature of the face appearing in a picture, and the temperature of the background appearing in the picture are the same (these temperatures are both the temperature of the picture). Similarly, the temperature of a face displayed on a display device and the temperature of the background displayed on the display device are the same (these temperatures are both the temperature of the display device). The temperature of the face of a doll is different from the temperature of a face that is a living body; the temperature of the face of a doll in many cases approaches the temperature of around the face (the background) or may be lower than the temperature of around the face.

The above-described configuration of the biometric determination device 100 allows for determining with high accuracy whether or not a face is a living body, and preventing a face authentication breach by taking as the determination reference whether or not the temperature of a face region is higher than the temperature of the extra-facial region by greater than or equal to a predetermined threshold. Specifically, a determination can be made that the face is a non-living body even if any of a picture or video, a doll, etc., is used for spoofing, making it possible to prevent a face authentication breach. Though it is conceivable to also have a configuration that determines whether or not the face is a living body from only the temperature of the face, it is conceivable that the temperature of the face is considerably impacted by the temperature around the face. Therefore, a highly accurate biometric determination can be performed with a configuration that employs the temperature of the face and the temperature around the face than a configuration that employs only the temperature of the face.

Embodiment

An embodiment of the present invention is described below.

Figure 2:
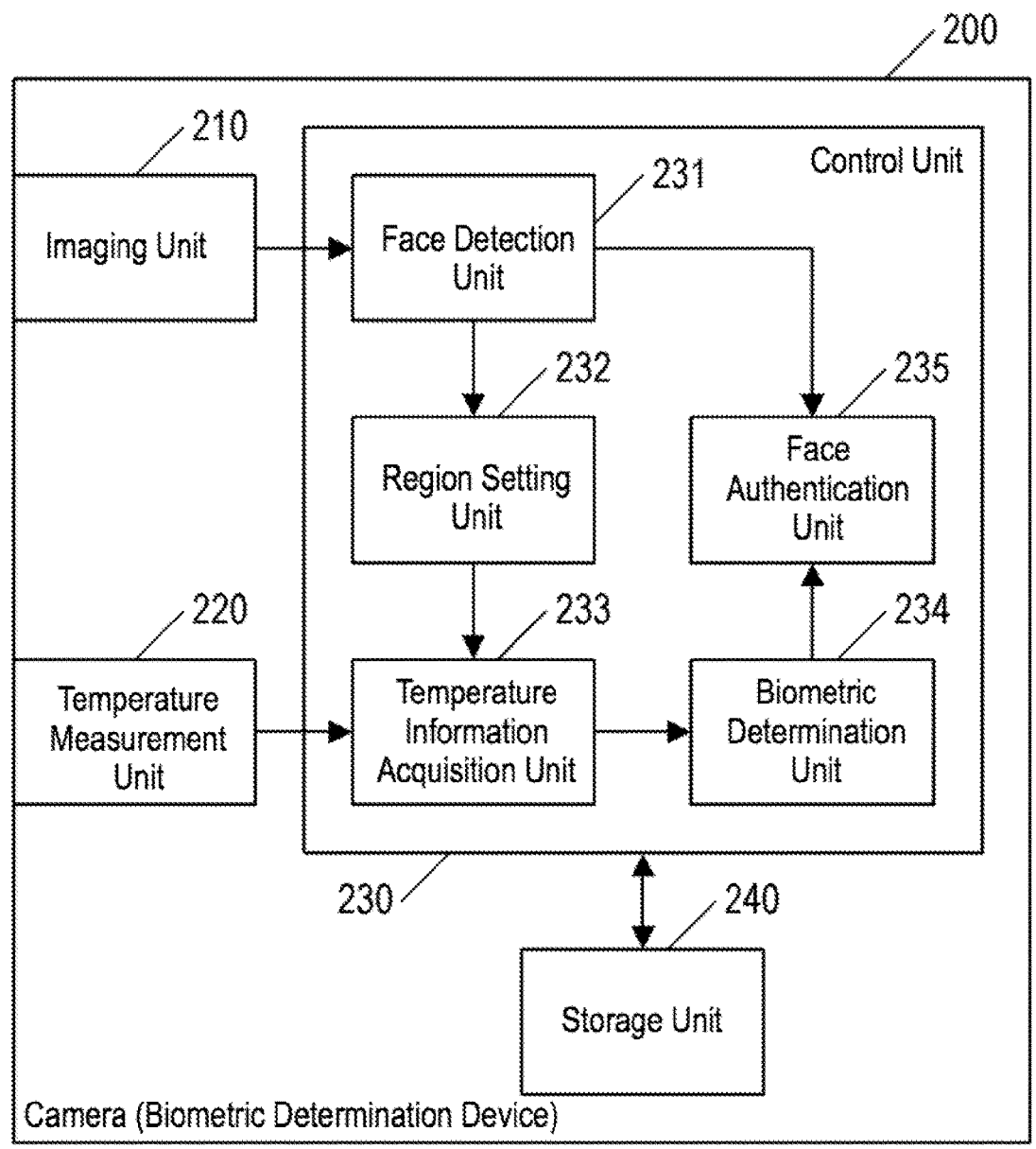
FIG. 2 is a block diagram illustrating an example configuration of a camera in an embodiment of the present invention.

FIG. 2 is a block diagram illustrating an example configuration of a camera 200 (biometric determination device; face authentication device) according to this embodiment; the camera 200 includes an imaging unit 210, a temperature measurement unit 220, a control unit 230, and a storage unit 240. The control unit 230 includes a face detection unit 231, a region setting unit 232, a temperature information acquisition unit 233, a biometric determination unit 234, and a face authentication unit 235.

The imaging unit 210 is an imaging sensor such as a CCD, or CMOS, and performs imaging, and outputs the imaging result (the image captured) to the control unit 230 (face detection unit 231).

The temperature measurement unit 220 is a thermal sensor or the like, and performs measurement of the temperature of each location and outputs the measurement results (information on the temperature distribution; information representing the temperature of each location) to the control unit 230 (the temperature information acquisition unit 233). The temperature measurement unit 220 measures, for instance, the temperature of locations in a range captured by the imaging unit 210.

The control unit 230 contains a central processing unit (CPU), random access memory (RAM), read only memory (ROM), etc., and performs control of each of the configuration elements or various information processing, or the like.

The face detection unit 231 detects a face from an image captured by the imaging unit 210 and outputs the detection result to a region setting unit 232 and the face authentication unit 235. The face detection unit 231 is one example of a detection unit of the present invention. Any kind of algorithm may be used for the face detection. As an example, the face may be detected by existing face detection techniques; more specifically, a face detector that incorporates image features such as HoG or Haar-like features and boosting may be employed in detecting the face. A learned model generated in accordance with existing machine learning techniques may be employed in detecting the face; more specifically, a learned model generated by deep learning techniques (e.g., R-CNN, Fast R-CNN, YOLO, SSD, etc.) may be employed in detecting the face.

The region setting unit 232 establishes the extra-facial region, which is a region around the face region, on the basis of the detection result from the face detection unit 231 (more specifically, the face region is the region of the face detected by the face detection unit 231). The region setting unit 232 outputs information on the face region and information on the extra-facial region (region information) to the temperature information acquisition unit 233. The region setting unit 232 is one example of a setting unit of the present invention.

The method for establishing the extra-facial region is not particularly limited; however, the region setting unit 232 may establish the extra-facial region as illustrated in FIGS. 3A to 3D, and FIGS. 4A and 4B. FIGS. 3A to 3D, and FIGS. 4A and 4B each illustrates an example of images captured by the imaging unit 210.

Figure 3A:
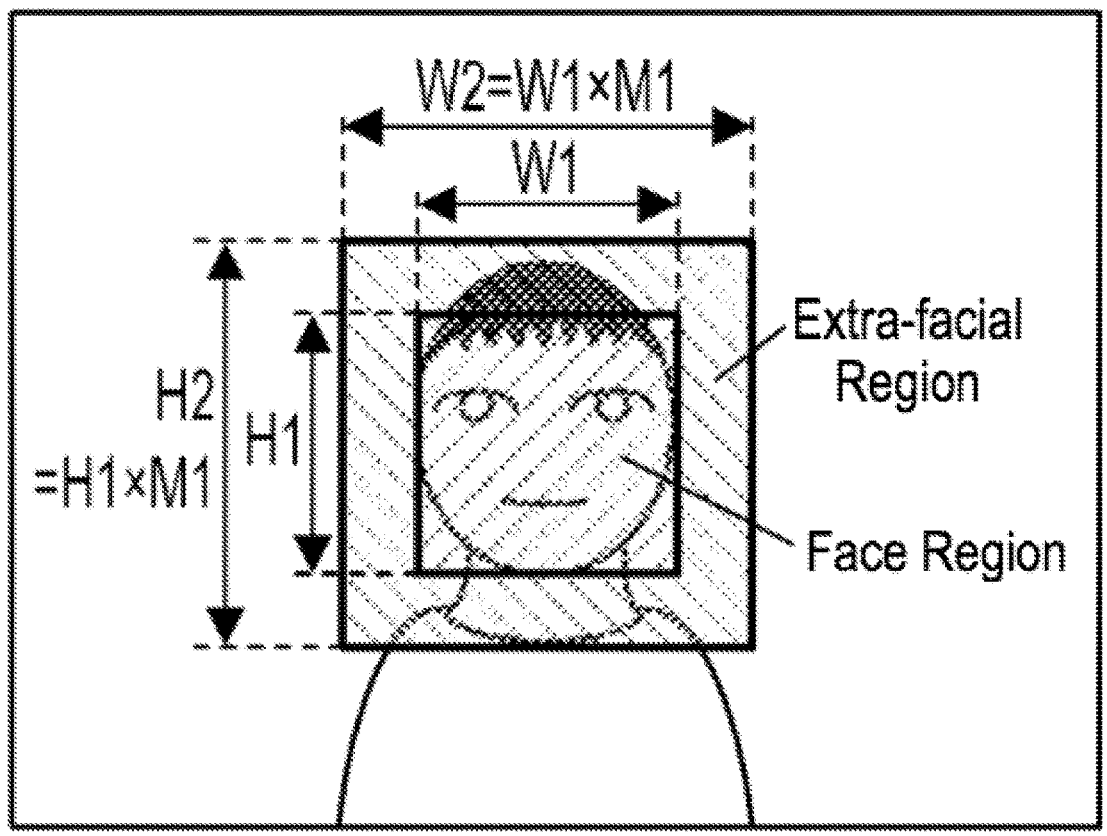
FIGS. 3A to 3D each illustrates an example of a captured image according to an embodiment of the present invention.

FIG. 3A illustrates an example of a case where the face region is a rectangular region, and illustrates the region setting unit 232 establishing the extra-facial region on the basis of a face region of a height H1 and a width W1. In FIG. 3A, the extra-facial region is set as a region that excludes the face region from a rectangular region that is centered on the face region and is an enlargement of the face region such that the height H2 of the rectangular region and the width W2 of the rectangular region are each a predetermined multiple (magnification M1) of the face region. That is, the extra-facial region is set by excluding the face region from a rectangular region that is centered on the face region and is a height H2=H1×M1 and a width W2=W1×M1.

Figure 3B:
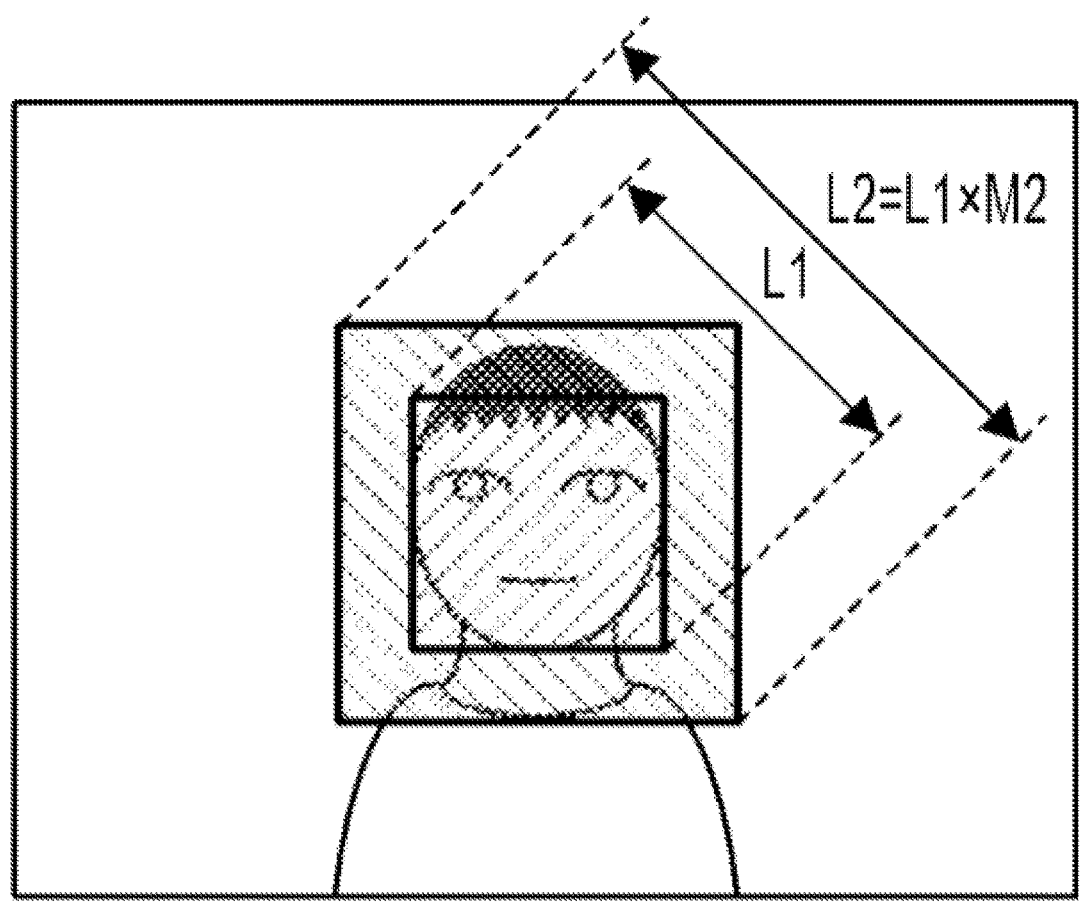

FIG. 3B illustrates an example of a case where the face region is a rectangular region, and illustrates the region setting unit 232 establishing the extra-facial region on the basis of a diagonal of length L1 of the face region. In FIG. 3B, the extra-facial region is set as a region that excludes the face region from a rectangular region centered on the face region and is an enlargement of the face region such that the length L2 of a diagonal of the rectangular region is a predetermined multiple (magnification M2) of the face region. That is, the extra-facial region is set by excluding the face region from a rectangular region that is centered on the face region and has a diagonal of length L2=L1×M2.

Figure 4A:
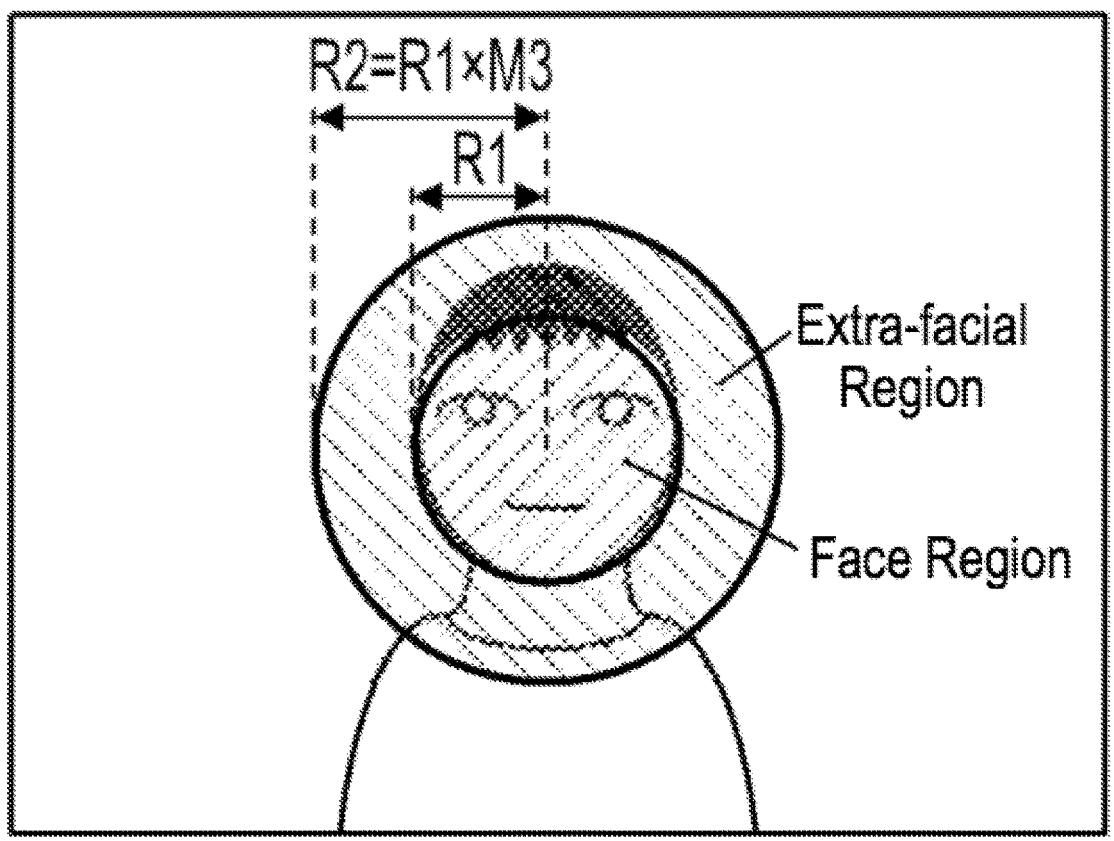
FIGS. 4A and 4B each illustrates an example of a captured image according to an embodiment of the present invention.

FIG. 4A illustrates an example of a case where the face region is a circular region, and illustrates the region setting unit 232 establishing the extra-facial region on the basis of a face region of radius R1. In FIG. 4A, the extra-facial region is set as a region that excludes the face region from a circular region that is centered on the face region and is an enlargement of the face region such that the radius R2 of the circular region is a predetermined multiple (magnification M3) of the face region. That is, the extra-facial region is set by excluding the face region from a circular region that is centered on the face region and has a radius $R2=R1 \times M3$.

Figure 3C:
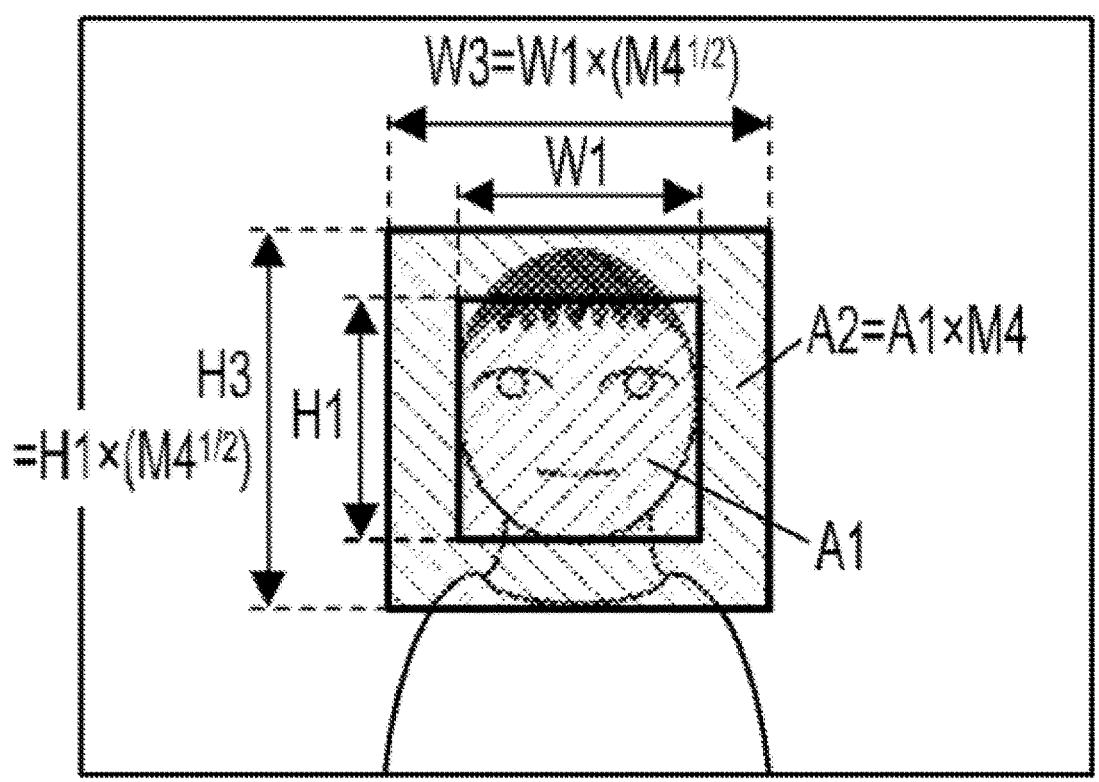
Figure 4B:
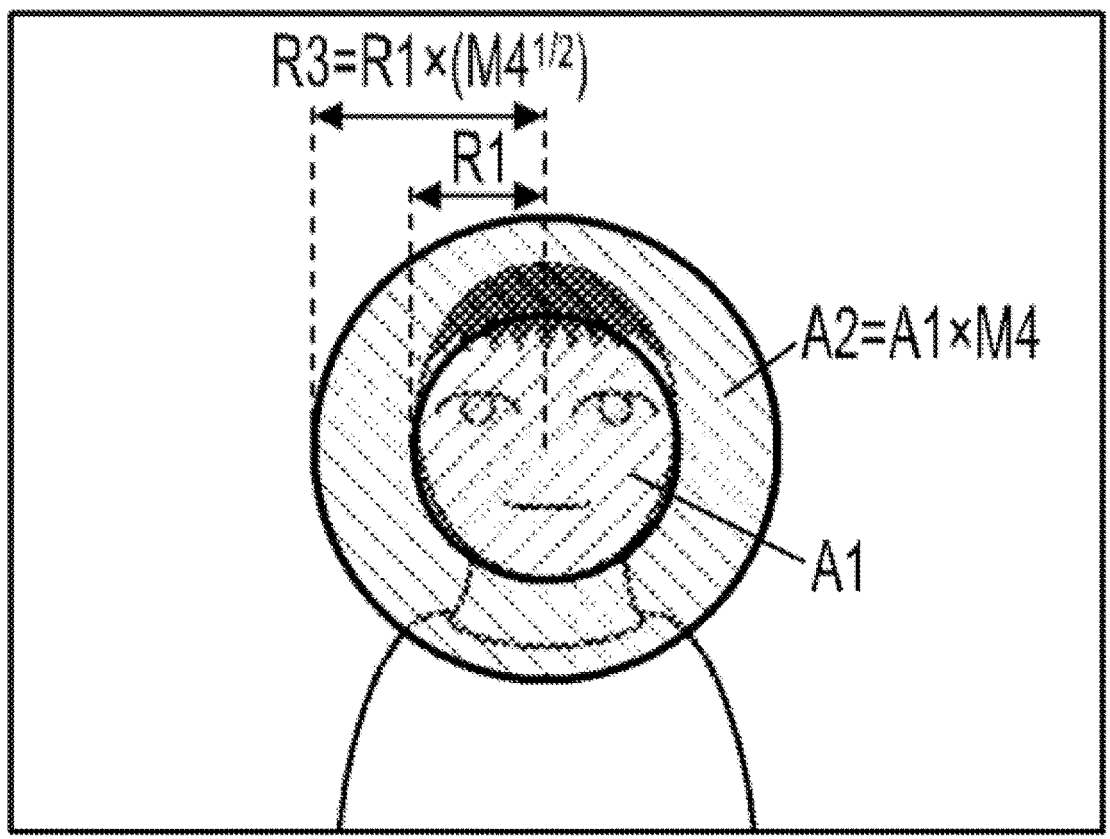

FIG. 3C and FIG. 4B illustrate examples of the region setting unit 232 establishing the extra-facial region on the basis of the area A1 of the face region. In FIG. 3C and FIG. 4B, the extra-facial region is set as a region that excludes the face region from a region that is centered on the face region and is an enlargement of the face region such that the area A2 of the region is a predetermined multiple (magnification M4) of the face region. In FIG. 3C where the face region is a rectangular region, the extra-facial region is set by excluding the face region from a rectangular region that is centered on the face region and is a height $H3=H1 \times (M4^{1/2})$ M1 and a width $W3=W1 \times (M4^{1/2})$ M1. In FIG. 4B where the face region is a circular region, the extra-facial region is set by excluding the face region from a circular region that is centered on the face region and has a radius $R3=R1 \times (M4^{1/2})$.

FIGS. 3A to 3C, FIGS. 4A and 4B illustrate examples where the region surrounding the face is established as the extra-facial region. However, when the extra-facial region is so established, the extra-facial region contains the head portion that is at the upper part of the face region and the neck portion that is at the lower part of the face region; the head portion and neck portion may influence the temperature of the extra-facial region, with a temperature that is offset from the temperature of the background being used as the temperature of the extra-facial region. Therefore, the region setting unit 232 may establish two regions located on the left and the right of the face region, as illustrated in FIG. 3D to serve as the extra-facial region.

Figure 3D:
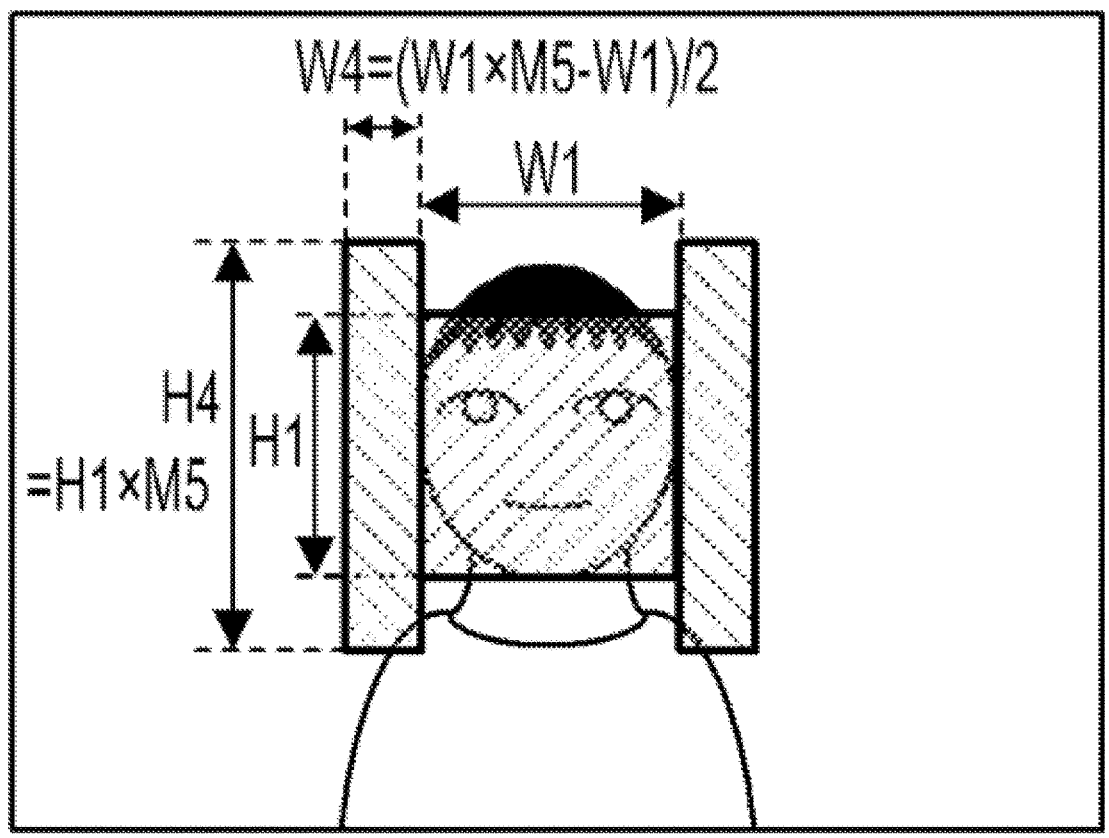

FIG. 3D illustrates an example of a case where the face region is a rectangular region, and illustrates the region setting unit 232 establishing the extra-facial region on the basis of a face region of a height H1 and a width W1. In FIG. 3D, two regions, adjacent on the left and the right of the face region are established as the extra-facial region. These two regions are two rectangular regions obtained by excluding the face region and a rectangular region of the face region that has the same width W1 as the upper part of said face region and a rectangular region of the face region that has the same width W1 as the lower part of said face region from a rectangular region that is an enlargement of the face region by a predetermined multiple. In FIG. 3D the rectangular region which is an enlargement of the face region by a predetermined multiple is a rectangular region resulting from enlarging the height H1 and the width W1 of the face region by a magnification M5. Accordingly, the region that is adjacent to the right side of the face region and the region that is adjacent to the left side of the face region are both rectangular regions of height $H4=H1 \times M5$ and width $W4=(W1 \times M5-W1)/2$.

Herewith the head portion and the neck portion can be excluded from the extra-facial region, and a temperature closer to the temperature of the background may be employed. As a result, the determination of whether or not a face is a living body can be made with even higher accuracy, and face authentication can be performed with even higher accuracy. Specifically, this can prevent an erroneous determination that a face that is a living body is a non-living body, thus preventing a failure of proper face authentication using the face of a living body.

The rectangular region in FIG. 3D, which is an enlargement of the face region by a predetermined multiple, is an example of a rectangular region resulting from enlarging the height and the width of the face region by a predetermined multiple. However, the rectangular region is not limited thereto. The rectangular region, which is an enlargement of the face region by a predetermined multiple, may be an enlargement of length of a diagonal of the face region by a predetermined multiple, or an enlargement of the area of the face region by a predetermined multiple, or the like.

The various above-described magnifications (magnification M1 to M5) are not particularly limited, and may be two to three times, for instance. These magnifications may be established as desired by the user (by the administrator of the camera 200, etc.) or may be a fixed value.

The extra-facial region is not limited to the above region; a region distant from the face region may be established as an extra-facial region, or three or more regions may be established as extra-facial regions.

FIG. 2 is now described. The temperature information acquisition unit 233 acquires information on the temperature of the face region and the temperature of the extra-facial region (temperature information) on the basis of the measurement result from the temperature measurement unit 220 (information on the temperature distribution) and region information output from the region setting unit 232 (information on the face region and the extra-facial region). The temperature information acquisition unit 233 outputs the temperature information to the biometric determination unit 234. The temperature information acquisition unit 233 is one example of an acquisition unit of the present invention. Here, the temperature of the face region is a temperature representing the face region (representative temperature), and in this embodiment is the mean temperature of the face region (a mean of a plurality of temperatures each corresponding to a plurality of locations in the face region). The temperature of the extra-facial region is similarly a temperature representing the extra-facial region (representative temperature), and in this embodiment is the mean temperature of the extra-facial region (a mean of a plurality of temperatures each corresponding to a plurality of locations in the extra-facial region).

The representative temperature is not limited to a mean temperature. The temperature of the face region may be the mode or median of a plurality of temperatures each corresponding to a plurality of locations in the face region. The temperature of the extra-facial region may be the mode or median of a plurality of temperatures each corresponding to a plurality of locations in the extra-facial region. The mean, mode, median and the like which correspond to a representative temperature may be employed, whereby whether or not a face is a living body may be determined with even higher accuracy, and face authentication may be performed with even higher accuracy. Thus, there is no longer the need to use the temperature of an object placed on the face (e.g., such as glasses put on the face), and the like, as the temperature of the face region, or the temperature of a heat source around the face (e.g., lighting) and the like as the temperature of the extra-facial region, for example. As a result, this can prevent an erroneous determination that a face that is a living body is a non-living body, preventing a failure of proper face authentication using the face of a living body. The definition of the representative temperatures for the face region and the extra-facial region may be differentiated so that the representative temperature of the face region corresponds to a mean, and the representative temperature of the extra-facial region corresponds to a mode.

The biometric determination unit 234 determines whether or not the face detected by the face detection unit 231 is a living body on the basis of the temperature information acquired by the temperature information acquisition unit 233. Specifically the biometric determination unit 234 determines that the face detected is a living body when the temperature of the face region is higher than the temperature of the extra-facial region by greater than or equal to a predetermined threshold, and that the face detected is not a living body when the temperature of the face region is not higher than the temperature of the extra-facial region by greater than or equal to a predetermined threshold. The biometric determination unit 234 outputs the result of the biometric determination (information on whether or not the face detected is a living body) to the face authentication unit 235. The biometric determination unit 234 is one example of a determination unit of the present invention. The predetermined threshold may be established as desired by the user or may be a fixed value.

The face authentication unit 235 performs face authentication on the basis of a detection result from the face detection unit 231 (information on the face detected) and the determination result from the biometric determination unit 234 (information on whether or not the face detected is a living body). More specifically, the storage unit registers face information for the purpose of face authentication (face information that is compared to a detected face, face image, etc.). The face authentication unit 235 performs the following processing when the face detected by the face detection unit 231 is a living body. When the face information of only one person can be registered, the face authentication unit 235 determines whether or not the face that is detected and the face information registered in the storage unit 240 are a match (matching process). The face authentication unit 235 takes a match as a successful authentication and takes no match as a failed authentication. When a plurality of face information each corresponding to a plurality of persons can be registered, the face authentication unit 235 searches among the plurality of face information for the face information matching the face detected. The face authentication unit 235 takes the presence of matching face information as a successful authentication for the person corresponding to aforesaid face information, and takes the absence of matching face information as a failed authentication. When the face detected by the face detection unit 231 is not a living body, the face detection unit 231 takes this as failed authentication without performing the above matching process based on the detection result from the face detection unit 231.

Any kind of algorithm may be used for the matching process. As an example, whether or not there is a match may be determined based on existing matching processes; more specifically, a comparator machine (authenticator machine) that incorporates image features such as HoG or Haar-like features and boosting may be employed in determining whether or not there is a match. A learned model generated in accordance with existing machine learning techniques may be employed in determining whether or not there is a match. More specifically, a learned model generated by deep learning techniques (e.g., R-CNN, Fast R-CNN, YOLO, SSD, etc.) may be employed in determining whether or not there is a match.

The storage unit 240 may store a program executed by the control unit 230, or various kinds of data, etc., used by the control unit 230. The storage unit 240 may be an auxiliary storage device such as a hard drive, solid-state drive, or the like.

Though the camera 200 is taken as the biometric determination device of this embodiment, the biometric determination device may be a device that is separate from the camera 200 (e.g., a personal computer [PC]). The biometric determination device may include an interface for acquiring the imaging result from the imaging unit 210 (the image captured), or the imaging unit 210 may be provided in a device separate from the biometric determination device. Similarly, the biometric determination device may include an interface for acquiring the measurement result from the temperature measurement unit 220 (information on the temperature distribution), or the temperature measurement unit 220 may be provided in a device separate from the biometric determination device. When the imaging unit 210 is provided in a separate device from the biometric determination device, the biometric determination device and the device with the imaging unit 210 may be connected to each other via wire or wirelessly. When the temperature measurement unit 220 is provided in a separate device from the biometric determination device, the biometric determination device and the device with the temperature measurement unit 220 may be connected to each other via wire or wirelessly.

The place where the biometric determination device may be installed is also not limited. The biometric determination device may be installed in the same room as the imaging unit 210 or the temperature measurement unit 220, or not. The biometric determination device may be a cloud-based computer or not. The result of the biometric determination may also be used for a purpose other than face authentication, and the biometric determination device need not include the face authentication unit 235.

Figure 5:
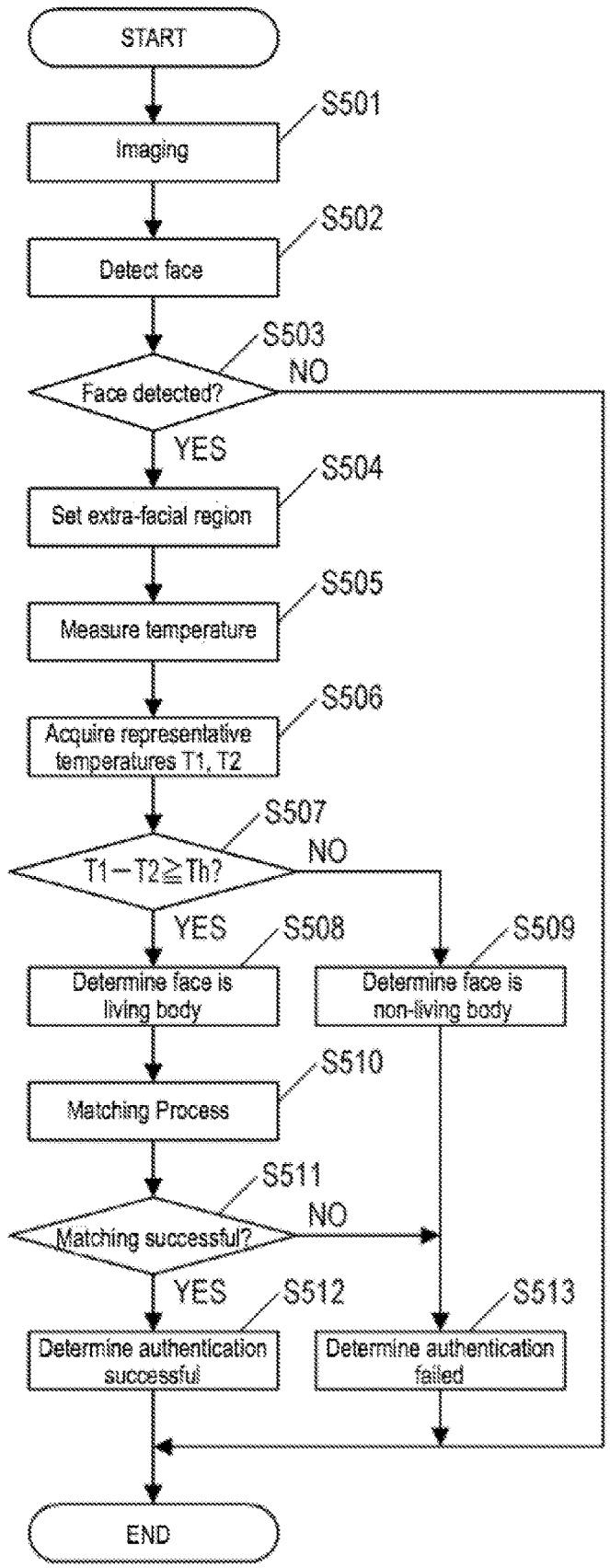
FIG. 5 is a flowchart illustrating an example of the processing flow in a camera according to an embodiment of the present invention.

FIG. 5 is a flowchart illustrating an example of the processing flow in the camera 200. In this embodiment, the camera 200 initiates the processing flow in FIG. 5 in accordance with an operation regarding the initiation of face authentication. The camera 200 may repeatedly execute the processing flow of FIG. 5. At this point, the repetition period for the processing flow of FIG. 5 is not particularly limited; for example, the processing flow of FIG. 5 may be repeated with the imaging frame rate of the imaging unit 210 (30 fps, etc.).

First, the imaging unit 210 performs imaging (step S501). The face detection unit 231 detects a face from the image captured in step S501 (step S502).

Next, the control unit 230 determines whether or not a face is detected in step S502 (step S503). When a face is detected (YES, step S503), processing continues to step S504. When no face is detected (NO, step S503), the camera 200 ends the processing flow of FIG. 5. At this point, a notification such as "Please bring the face closer to the camera", may be output in order to ensure that the face that is captured can be detected.

In step S504, the region setting unit 232 establishes the extra-facial region on the basis of the face region detected in step S502. The method of setting the extra-facial region is as above described. The temperature measurement unit 220 performs temperature measurement (step S505). The timing for performing temperature measurement is not particularly limited hereto, for example, the timing may coincide with step S501.

Next, the temperature information acquisition unit 233 acquires a representative temperature T1 of the face region detected in step S502, and a representative temperature T2 of the extra-facial region established in step S504 on the basis of the measurement result in step S505 (step S506). The representative temperature T1 may be the mean temperature of the face region, and the representative temperature T2 may be the mean temperature of the extra-facial region, for instance.

The biometric determination unit 234 determines whether or not the representative temperature T1 of the face region is higher than the representative temperature T2 of the extra-facial region by greater than or equal to a predetermined threshold Th; that is, the biometric determination unit 234 determines whether or not a conditional formula T1−T2≥Th is satisfied (step S507). When the representative temperature T1 is higher than the representative temperature T2 by greater than or equal to the predetermined threshold Th, that is, when the conditional formula T1−T2≥Th is satisfied (YES, step S507), processing continues to step S508. When the representative temperature T1 is not higher than the representative temperature T2 by greater than or equal to the predetermined threshold Th, that is, when the conditional formula T1−T2≥Th is not satisfied (NO, step S507), processing continues to step S509.

In step S508, the biometric determination unit 234 determines that the face detected in step S502 is a living body. The processing then continues to step S510.

In step S509, the biometric determination unit 234 determines that the face detected in step S502 is a non-living body. The processing then continues to step S513.

In step S510, the face authentication unit 235 performs a matching process on the basis of the detection result from step S502. The matching process is as above described.

In step S511, the face authentication unit 235 determines whether or not the matching process of step S520 was successful; that is, the face authentication unit 235 determines whether or not the face information that matches the face detected in step S502 is registered in the storage unit 240. When the matching process is successful (YES, step S511), that is, when face information is registered that matches the face detected, processing continues to step S512. When the matching process is a failure (NO, step S511), that is, when the no face information is registered that matches the face detected, processing continues to step S513.

In step S512, the face authentication unit 235 determines a successful authentication. The camera 200 then ends the processing flow of FIG. 5.

In step S513, the face authentication unit 235 determines a failed authentication. The camera 200 then ends the processing flow of FIG. 5.

As above described, this embodiment allows for determining with high accuracy whether or not a face is a living body, and preventing a face authentication breach by taking as the determination reference whether or not the temperature of a face region is higher than the temperature of the extra-facial region by greater than or equal to a predetermined threshold.

Figure 6:
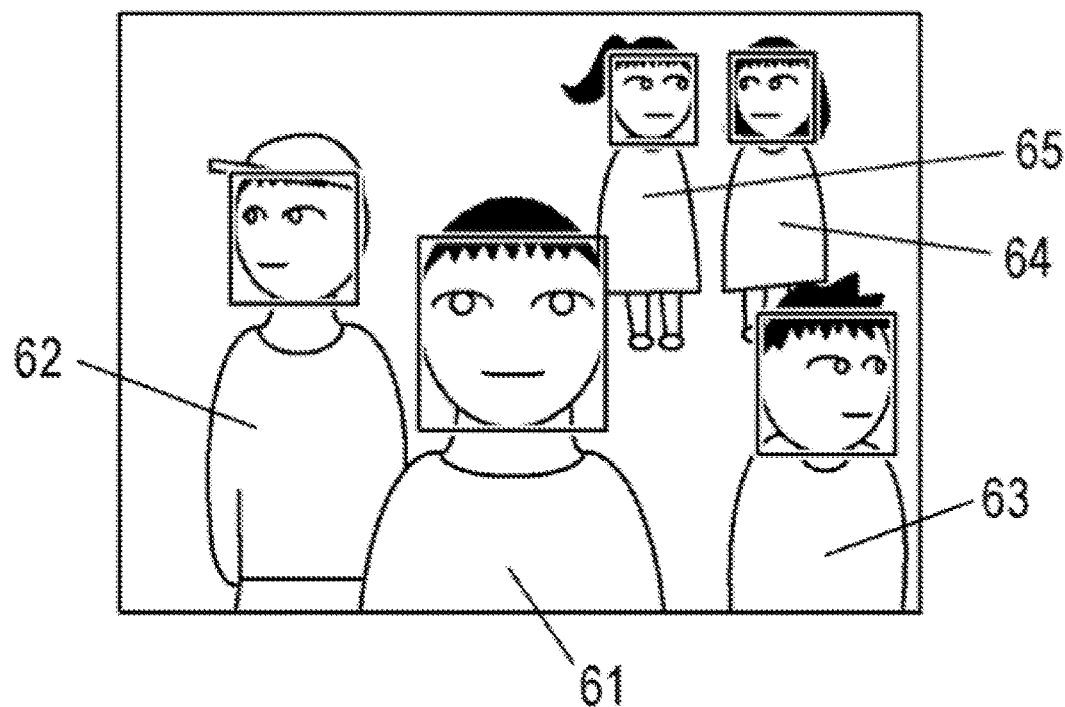
FIG. 6 illustrates an example of a captured image according to an embodiment of the present invention.

As illustrated in FIG. 6, the face detection unit 231 may detect a plurality of faces in some cases. FIG. 6 is one example of an image captured by the imaging unit 210, and persons 61-65 appear in the image in FIG. 6. The person 61 is a face-based registrant (a person whose face information is registered for the purpose of face authentication) who is about to perform face authentication, the person 62 is a face-based registrant who is not attempting face authentication, and the persons 63-65 are persons who are not face-based registrants. In this case, the processing may be as follows.

The acquisition of temperature information by the temperature information acquisition unit 233, the biometric determination by the biometric determination unit 234, and the face authentication by the face authentication unit 235 may be performed with regard to each of the plurality of faces, for instance. Herewith, the failure of face authentication for a face-based registrant can be prevented in situation where, for instance, the face-based registrant stands in front of a poster where a face appears or the face-based registrant is with a plurality of persons or a doll (the situation in FIG. 6), etc. That is, the face-based registrant 61 who is about to perform face authentication can do so successfully without issue. However, even a face-based registrant 62 who is not about to perform face authentication could be authenticated successfully.

A face-based registrant who is about to perform face authentication tends to bring their face close to the camera 200, and (as illustrated in FIG. 6) the face of aforesaid face-based registrant tends to appear very large within the image captured. Therefore, the acquisition of temperature information by the temperature information acquisition unit 233, the biometric determination by the biometric determination unit 234, and the face authentication by the face authentication unit 235 may be performed with regard to the face that is the largest among the plurality of faces. Herewith, the failure of face authentication for a face-based registrant can be prevented in situation where, for instance, the face-based registrant stands in front of a poster where a face appears or the face-based registrant is with a plurality of persons or a doll (the situation in FIG. 6), etc. That is, the face-based registrant 61 who is about to perform face authentication can do so successfully without issue. Moreover, successful face authentication can be prevented for the face-based registrant who is not about to perform face authentication, further improving the level of security of the face authentication. Acquiring the temperature information and the biometric determination are limited to a specific face, thus also reducing the processing load.

A face-based registrant who is about to perform face authentication tends to face front at the camera 200 and the face of aforesaid face-based registrant tends to appear at the center portion of the image captured (the situation illustrated in FIG. 6). Therefore, the acquisition of temperature information by the temperature information acquisition unit 233, the biometric determination by the biometric determination unit 234, and the face authentication by the face authentication unit 235 may be performed with regard to the face that is closest to the center of the image among the plurality of faces. Herewith, the failure of face authentication for a face-based registrant can be prevented in situation where, for instance, the face-based registrant stands in front of a poster where a face appears or the face-based registrant is with a plurality of persons or a doll (the situation in FIG. 6), etc. That is, the face-based registrant 61 who is about to perform face authentication can do so successfully without issue. Moreover, successful face authentication can be prevented for the face-based registrant who is not about to perform face authentication, further improving the level of security of the face authentication. Acquiring the temperature information and the biometric determination are limited to a specific face, thus also reducing the processing load.

A face-based registrant who is about to perform face authentication tends to direct their gaze toward the camera. Therefore, the acquisition of temperature information by the temperature information acquisition unit 233, the biometric determination by the biometric determination unit 234, and the face authentication by the face authentication unit 235 may be performed with regard to the face that has the gaze directed toward the camera 200 among the plurality of faces. The gaze may be detected using existing processes. Herewith, the failure of face authentication for a face-based registrant can be prevented in situation where, for instance, the face-based registrant stands in front of a poster where a face appears or the face-based registrant is with a plurality of persons or a doll (the situation in FIG. 6), etc. That is, the face-based registrant 61 who is about to perform face authentication can do so successfully without issue. It is also possible to prevent face authentication from being successful when unnecessary when a face-based registrant is near the camera 200 without gazing at the camera 200 (contrary to the intent of the face-based registrant), further improving the level of security of the face authentication. In FIG. 6, it is possible to prevent successful face authentication of a face-based registrant 62 who is not about to perform face authentication. Acquiring the temperature information and the biometric determination are limited to a specific face, thus also reducing the processing load.

Additional Considerations

The above-described embodiment is merely for describing an example configuration of the present invention. The present invention is not limited to the specific form above described and may be modified in various ways within the scope of the technical ideas herein. The acquisition of temperature information by the temperature information acquisition unit 233, the biometric determination by the biometric determination unit 234, and the face authentication by the face authentication unit 235 may be performed with regard to a face satisfying a plurality of conditions among the plurality of faces, for example. The plurality of conditions may include any of the above-described "the largest face", "the face closest to the center of the image", and "the gaze directed to the camera".

Supplemental Note 1

A biometric determination device (100, 200) including: a detection unit (101, 231) configured to detect a face from an image captured;
  an acquisition unit (102, 233) configured to acquire information on the temperature of a face region, which is a region in which a face is detected by the detection unit, and the temperature of an extra-facial region, which is a region around the face region; and
  a determination unit (103, 234) configured to determine on the basis of information acquired by the acquisition unit that a face that is detected is a living body when the temperature of the face region is higher than the temperature of the extra-facial region by greater than or equal to a predetermined threshold, and that a face that is detected is not a living body when the temperature of the face region is not higher than the temperature of the extra-facial region by greater than or equal to the predetermined threshold.

Supplemental Note 2

A biometric determination method including: a detection step (S502) of detecting a face from an image captured;
  an acquisition step (S506) of acquiring information on the temperature of a face region, which is a region in which a face is detected during the detection step, and the temperature of an extra-facial region, which is a region around the face region; and
  a determination step (S507-S509) of determining on the basis of information acquired during the acquisition step that a face that is detected is a living body when the temperature of the face region is higher than the temperature of the extra-facial region by greater than or equal to a predetermined threshold, and that a face that is detected is not a living body when the temperature of the face region is not higher than the temperature of the extra-facial region by greater than or equal to the predetermined threshold.

REFERENCE SIGNS LIST

100: Biometric determination device
101: Face detection unit
102: Temperature information acquisition unit
103: Biometric determination unit
200: Camera
210: Imaging unit
220: Temperature measurement unit
230: Control unit
240: Storage unit
231: Face detection unit
232: Region setting unit
233: Temperature information acquisition unit
234: Biometric determination unit
235: Face authentication unit

The invention claimed is:

1. A biometric determination device comprising:
  a detection unit configured to detect a face from a captured image;
  an acquisition unit configured to acquire information on a temperature of a face region, which is a region in which the face is detected by the detection unit, and a temperature of an extra-facial region, which is a region around the face region;
  a determination unit configured to determine, on a basis of information acquired by the acquisition unit, that the face that is detected is a living body when the temperature of the face region is higher than the temperature of the extra-facial region by greater than or equal to a predetermined threshold, and that the face that is detected is not the living body when the temperature of the face region is not higher than the temperature of the extra-facial region by greater than or equal to the predetermined threshold; and
  a setting unit configured to set the extra-facial region on the basis of the face region,
  wherein the setting unit sets the extra-facial region as:
  (i) a region that excludes the face region, which is rectangular, from a rectangular region that is centered on the face region and is an enlargement of the face region such that a height of the rectangular region and a width of the rectangular region are a predetermined multiple of a height of the face region and a width of the face region, respectively;
  (ii) a region that excludes the face region, which is rectangular, from a rectangular region that is centered on the face region and is an enlargement of the face region such that a length of a diagonal of the rectangular region is a predetermined multiple of a length of a diagonal of the face region;
  (iii) a region that excludes the face region, which is circular, from a circular region that is centered on the face region and is an enlargement of the face region such that a radius of the circular region is a predetermined multiple of a radius of the face region;
(iv) a region that excludes the face region from a region that is centered on the face region and is an enlargement of the face region such that an area of the region that is centered on the face region is a predetermined multiple of an area of the face region; or
(v) two rectangular regions obtained by excluding the face region, which is rectangular, a rectangular region above the face region with the same width as an upper part of the face region, and a rectangular region below the face region with the same width as a lower part of the face region from a rectangular region that is centered on the face region and is an enlargement of the face region by a predetermined multiple.

2. The biometric determination device according to claim 1, wherein the temperature of the face region is a mean, mode, or median of a plurality of temperatures each corresponding to a plurality of locations in the face region; and
the temperature of the extra-facial region is a mean, mode, or median of a plurality of temperatures each corresponding to a plurality of locations in the extra-facial region.

3. The biometric determination device according to claim 1, wherein when a plurality of faces is detected by the detection unit, the acquisition of information by the acquisition unit and the determination by the determination unit are performed with regard to each of the plurality of faces.

4. The biometric determination device according to claim 1, wherein when a plurality of faces is detected by the detection unit, the acquisition of information by the acquisition unit and the determination by the determination unit are performed with regard to a face that is a largest among the plurality of faces.

5. The biometric determination device according to claim 1, wherein when a plurality of faces is detected by the detection unit, the acquisition of information by the acquisition unit and the determination by the determination unit are performed with regard to a face that is closest to a center of the captured image among the plurality of faces.

6. The biometric determination device according to claim 1, wherein when a plurality of faces is detected by the detection unit, the acquisition of information by the acquisition unit and the determination by the determination unit are performed with regard to a face, among the plurality of faces, that has a gaze directed toward a camera that captured the captured image.

7. A biometric determination method comprising:
a detection step of detecting a face from a captured image;
an acquisition step of acquiring information on a temperature of a face region, which is a region in which the face is detected in the detection step, and a temperature of an extra-facial region, which is a region around the face region; and
a determination step of determining, on a basis of information acquired during the acquisition step, that the face that is detected is a living body when the temperature of the face region is higher than the temperature of the extra-facial region by greater than or equal to a predetermined threshold, and that the face that is detected is not the living body when the temperature of the face region is not higher than the temperature of the extra-facial region by greater than or equal to the predetermined threshold; and
a setting step of setting the extra-facial region on the basis of the face region,
wherein the setting step sets the extra-facial region as:
(i) a region that excludes the face region, which is rectangular, from a rectangular region that is centered on the face region and is an enlargement of the face region such that a height of the rectangular region and a width of the rectangular region are a predetermined multiple of a height of the face region and a width of the face region, respectively;
(ii) a region that excludes the face region, which is rectangular, from a rectangular region that is centered on the face region and is an enlargement of the face region such that a length of a diagonal of the rectangular region is a predetermined multiple of a length of a diagonal of the face region;
(iii) a region that excludes the face region, which is circular, from a circular region that is centered on the face region and is an enlargement of the face region such that a radius of the circular region is a predetermined multiple of a radius of the face region;
(iv) a region that excludes the face region from a region that is centered on the face region and is an enlargement of the face region such that an area of the region that is centered on the face region is a predetermined multiple of an area of the face region; or
(v) two rectangular regions obtained by excluding the face region, which is rectangular, a rectangular region above the face region with the same width as an upper part of the face region, and a rectangular region below the face region with the same width as a lower part of the face region from a rectangular region that is centered on the face region and is an enlargement of the face region by a predetermined multiple.

8. A non-transitory computer readable medium storing a program for executing on a computer each of the steps in the biometric determination method according to claim 7.

* * * * *